United States Patent [19]
Rosengren

[11] Patent Number: 5,369,677
[45] Date of Patent: Nov. 29, 1994

[54] DEVICE FOR MATERIALS TESTING IN NUCLEAR REACTORS

[75] Inventor: Anders Rosengren, Västerås, Sweden
[73] Assignee: ABB Atom AB, Västerås, Sweden
[21] Appl. No.: 827,645
[22] Filed: Jan. 29, 1992
[30] Foreign Application Priority Data Feb. 19, 1991 [SE] Sweden .................. 9100488-7

[51] Int. Cl.$^5$ ............................. G21C 23/00
[52] U.S. Cl. .................... 376/340; 376/249; 376/245
[58] Field of Search ............ 376/340, 249, 245, 260

[56] References Cited

U.S. PATENT DOCUMENTS

| | | |
|---|---|---|
| 4,764,882 | 8/1988 | Braschel et al. ............ 376/249 |
| 4,987,367 | 1/1991 | Ishikawa et al. ............ 376/249 |
| 5,109,718 | 5/1992 | Gugel et al. ............... 376/249 |
| 5,112,566 | 5/1992 | Butzin et al. .............. 376/245 |

*Primary Examiner*—Donald P. Walsh
*Assistant Examiner*—Frederick H. Voss
*Attorney, Agent, or Firm*—Watson, Cole, Grindle & Watson

[57] ABSTRACT

A testing device for load-testing of specimens (3) in a nuclear reactor environment is attached to one of the pipes (1) of the reactor for conveying a first medium under pressure and provides a first space (14) in open communication with the pipe (1). In the first space (14) a movable pull rod (15) is arranged, one end of which is attached to one half (16) of a specimen (3) arranged in the space (14). The other end of the pull rod (15) is joined to a tensile force device capable of being influenced by the first medium for achieving a tensile stress in the specimen (3).

6 Claims, 4 Drawing Sheets

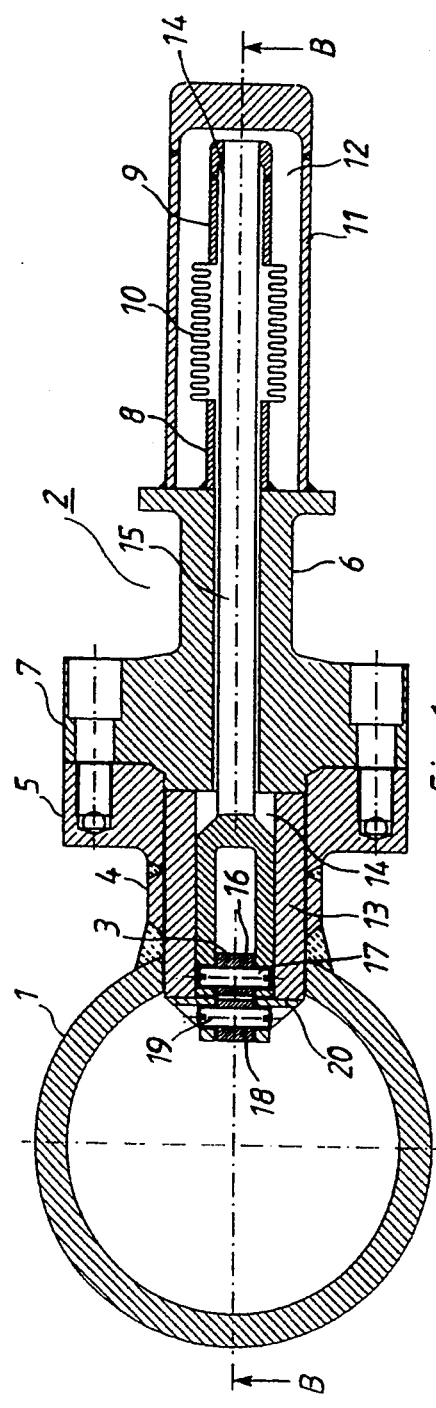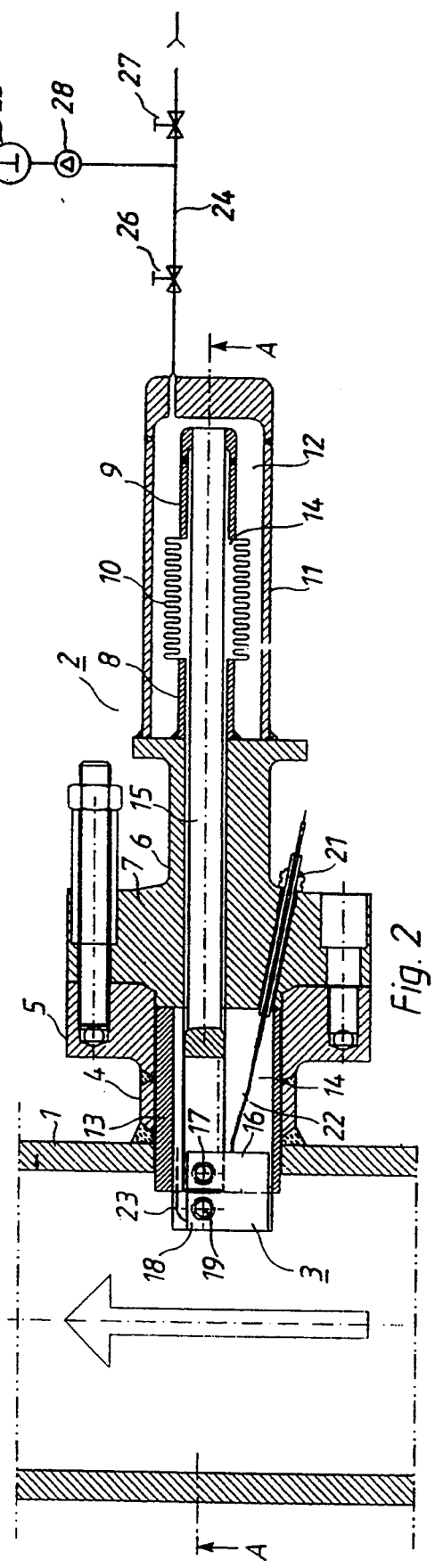

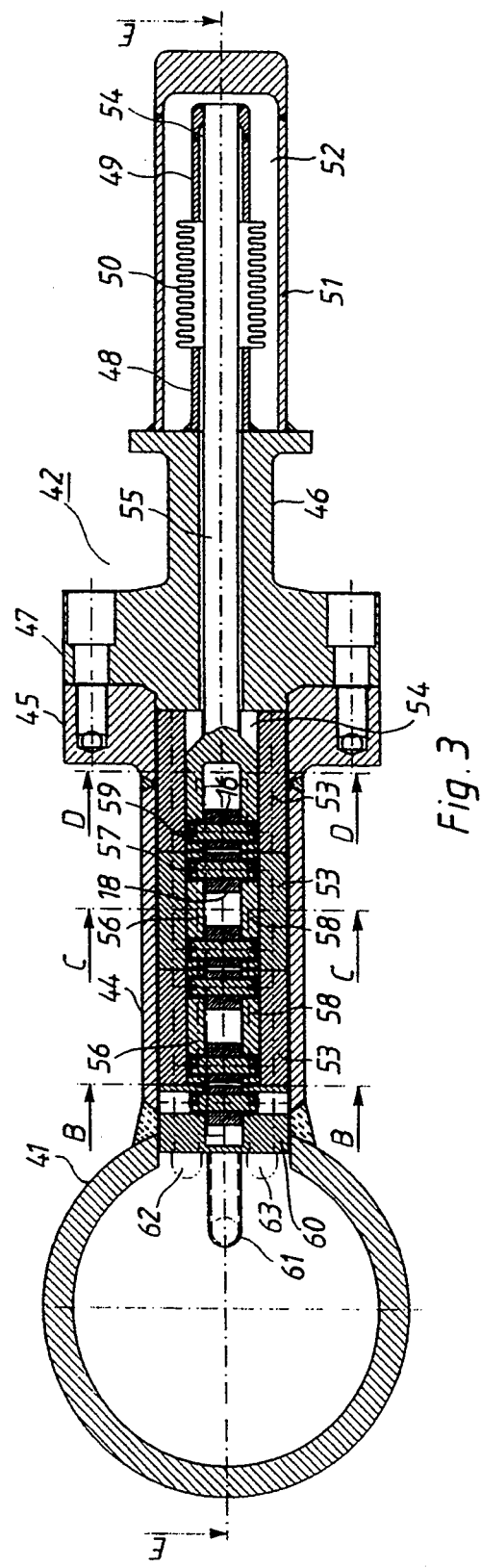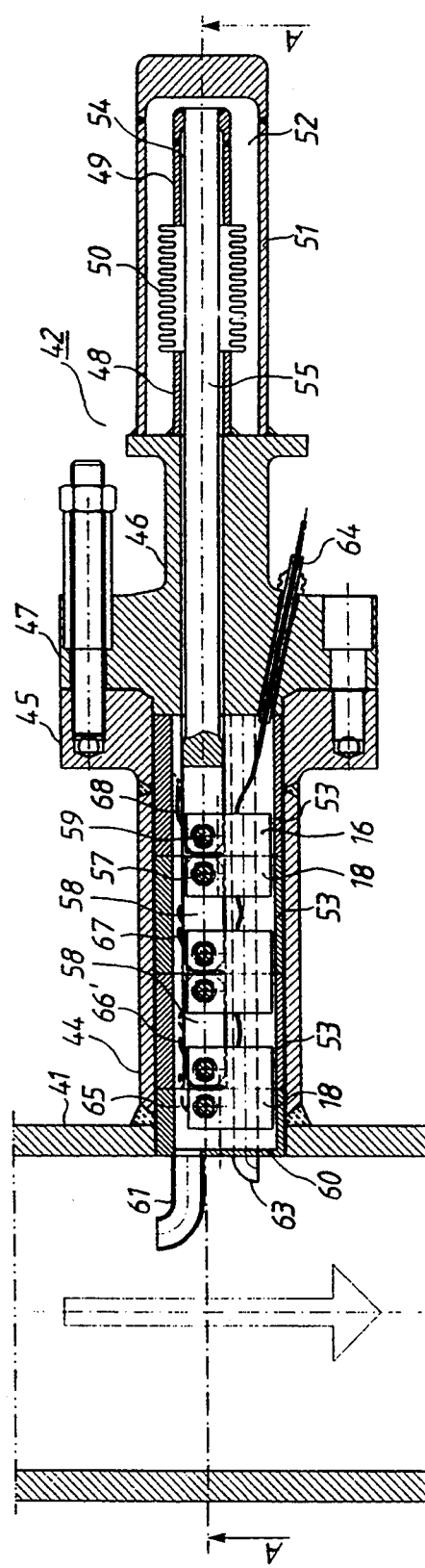

DEVICE FOR MATERIALS TESTING IN NUCLEAR REACTORS

BACKGROUND OF THE INVENTION

A material to be used in nuclear reactors is subjected to heavy stresses and must be carefully tested in a realistic environment before it can be put to use. Attempts have been made to simulate the real environment in which the material is to be used, but it is often difficult to imitate reality with all its varying parameters as regards pressure, vibrations, radioactivity, corrosion-producing media, etc. Nor have owners of nuclear power plants been particularly anxious to allow strength tests in situ in the nuclear power plants, due to the concern for expensive operational disturbances.

SUMMARY OF THE INVENTION

The present invention relates to a testing invention which should completely eliminate the above-mentioned apprehensions and consequently allow the testing of materials to take place directly in a realistic nuclear power environment.

The device is characterized in that a testing device is fixed to one of the pipes of a nuclear reactor for conveying a first medium under pressure. The testing device comprises a first space in open communication with the mentioned pipe and a movable pull rod, arranged in the first space, one end of which is intended to be fixed to one end of a specimen arranged in the space. The other end of the pull rod is joined to a tensile force device, capable of being influenced by the first medium, for achieving a tensile stress in the specimen via the pull rod. This testing device is formed as a completely closed polygon of forces and consequently does not load the pipe to which it is connected in the nuclear reactor. The load arrangement is fully passive, that is, the system pressure in the first medium mentioned provides the load on the specimen and no external devices for the load are required, which in turn means that the pull rod mentioned need not be passed through the wall of the reactor, which, of course, is of great importance. Further, the stochastic variations of the load will now directly influence the load device and hence the specimen via the system pressure.

The invention will be most readily understood with reference to the accompanying drawings.

BRIEF DESCRIPTION OF THE DRAWINGS

FIG. 1 is a section along line 1—1 of FIG. 2 showing the device mounted on a pipe conveying a first medium under pressure. The device shown is intended for a specimen.

FIG. 2 shows a section along line 2—2 of FIG. 1.

FIG. 3 is a section along line 3—3 of FIG. 4. The figure shows a device for several series-connected specimens.

FIG. 4 shows a section along line 4—4 of FIG. 3.

DETAILED DESCRIPTION OF THE PREFERRED EMBODIMENTS

Figure 7:
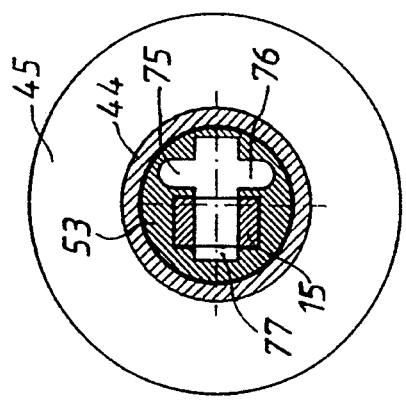
FIG. 7 shows a section along line 7—7 of FIG. 3.

In FIG. 1, 1 designates a pipe in, for example, a nuclear reactor. The pipe 1 conveys a first medium which may be gaseous and may be under a high pressure (100 bar). To this pipe 1 the testing device 2 for loading of a specimen 3 has been fixed. A hole has been made in the pipe 1 and around this a pipe socket 4 with a flange 5 has been welded. On this flange 5, a pipe socket 6 with a flange 7 is detachably mounted. At the other end of the pipe socket 6, a pipe socket 8 is welded. In the extension of the pipe socket 8, a tubular second sleeve 9 is arranged. In FIG. 1, the pipe socket 8 and the sleeve 9 are pressure-tightly interconnected by means of a bellows 10 of metal. The bellows 10 may be made of Inconel. The pipe socket 8, the bellows 10 and the sleeve 9 are surrounded by a third sleeve 11 forming a second space 12 therearound these. Inside the pipe socket 4 there is arranged a spacing sleeve 13. The spacing sleeve 13, the pipe socket 6 and the pipe socket 8 together form a first sleeve. This first sleeve along with the second sleeve 9 surround at least part of a first space 14. In this space 14 a movable pull rod 15 is positioned and fixed at the end of the movable second sleeve 9. At its other end the pull rod 15 is fork-shaped, and between the forks one half 16 of the specimen 3 is fixed by means of a pin 17. The other half 18 of the specimen 3 is fixed by means of a pin 19 in the counter-support 20 which rests against the spacing sleeve 13.

In FIG. 2 the corresponding designations have been introduced. FIG. 2 also shows an electrical bushing 21. To indicate a rupture in the specimen 3, an electric current is passed through the specimen through the conductors 22 and 23, the conductor 23 being passed out of the testing device 2 through a bushing (not shown). If the specimen 3 is pulled into two parts, the current is, and this can suitably be indicated on a voltmeter (not shown).

The second space 12 may either be completely closed and thus only have normal atmospheric pressure, or be connectable via a conduit 24 either to a pressure source 25 or to atmospheric pressure. 26 and 27 designate stop cocks and 28 a non-return valve. The pressure source 25 may contain a medium with the same or a higher pressure in relation to the mentioned first medium in the pipe 1.

Figure 8:
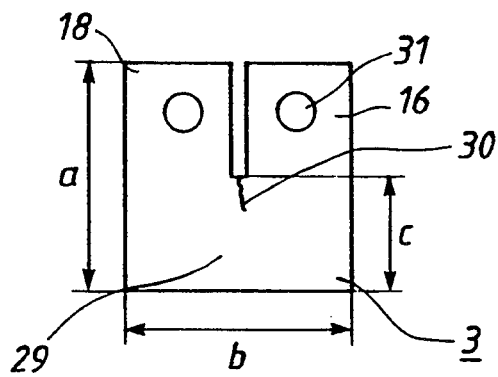
FIG. 8 shows a specimen.

The specimen 3 used is shown in FIG. 8. The specimen 3 is divided into two halves 16, 18 which are joined by means of a waist portion 29, in which an approximately 10 mm deed crack 30 is initiated. In each half 16, 18 there is a through-hole 31 for fixing the specimen 3 in the testing device 2. The dimensions of the specimen 3 are chosen such that a=60 mm, b=50 mm and c=30 mm. The thickness of the specimen 3 may be set at 25 mm.

The testing device 2 operates as follows. The part which is detachable from the flange 5, comprising the pipe socket 6 and the flange 7 and members connected thereto, such as the pull rod 15 and the spacing sleeve 13, is provided outside the nuclear reactor with the specimen 3 to be tested. Thereafter, that part of the testing device 2 is inserted in position in the nuclear reactor and screwed to the flange 5. The pressure-carrying first medium in the pipe 1 is now given access to the first space 14 in the testing device 2. Since the second space 12 only has atmospheric pressure, the pull rod 15 will load the specimen with a force which becomes approximately equal to the pressure of the first medium (the system pressure) times the cross-sectional area of the bellows 10. The specimen 3 can also be relieved by connecting the space 12 to a pressure source with the same or a higher pressure than the system pressure.

In loaded condition, the specimen 3 is now subjected to all the stresses and pressure variations to which a material in a nuclear reactor is normally subjected, and the test therefore becomes very realistic. After a certain predetermined time, the specimen 3 together with the detachable part of the test device 2 is taken out and examined. For the material to be approved, the crack 30 already present at the beginning of the test must not have grown more than, for example, 10 mm. If the specimen were to be pulled into two parts during the testing, this is indicated electrically on, for example, the voltmeter outside the nuclear reactor. The specimen 3 and other parts, for example the counter-support 20 and the spacing sleeve 13, must of course be secured to the testing device 2 in such a way that a possible rupture in the specimen 3 will not cause some part to become detached and fall down into the pipe 1.

FIGS. 3-7 show an alternative embodiment of the testing device, here designated 42, intended for testing a plurality of specimens 3 arranged in series.

In FIG. 3, 41 designates a pipe in a nuclear reactor. As earlier, the pipe 41 conveys a first medium which is under a high pressure. To this pipe 41 the testing device 42 has been fixed by means of a pipe socket 44 with a flange 45. On the flange 45, a pipe socket 46 with a flange 47 is detachably mounted. To the other end of the pipe socket 46, a pipe socket 48 is welded. In the extension of the pipe socket 48, a movable second sleeve 49 is arranged. The pipe socket 48 and the sleeve 49 are pressure-tightly connected by means of a bellows 50 of metal. The pipe socket 48, the bellows 50 and the sleeve 49 are surrounded by a third sleeve 51 which forms a second space 52 around these. Inside the pipe socket 44, spacing sleeves 53 are arranged. The spacing sleeves 53, the pipe socket 46 and the pipe socket 48 together form a first sleeve. This first sleeve along with the second sleeve 49 surround at least part of a first space 54. In this space 54, a movable pull rod 55 is placed and fixed at the end of the movable second sleeve 49. At its other end, the pull rod 55 is fork-shaped and between the forks, one half 16 of a first specimen 3 is fixed by means of a pin 59. The other half 18 of the specimen 3 is fixed by means of a pin 57 in two links 56 and 58, which join the first specimen 3 to a second specimen 3. In this way, two or more specimens 3 may be tested at the same time in the testing device 2. In this case it is a question of three specimens 3 which are connected in series to the counter-support 60. To secure that the first pressure medium is passed into the first space 54 and passed out therefrom, respectively, the pitot tubes 61, 62 and 63 are arranged in the pipe 41.

Figure 9:
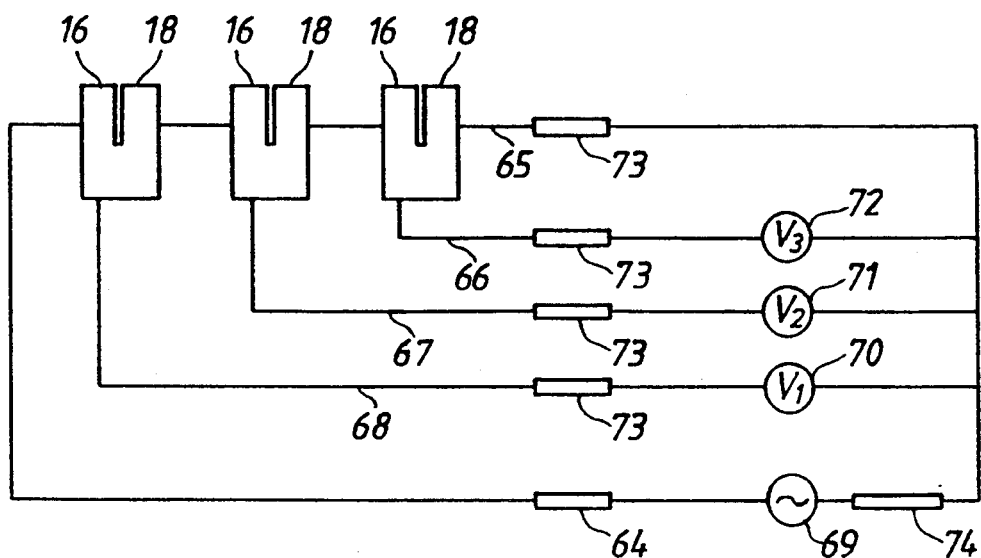
FIG. 9 shows a diagram of the electrical indication rupture in one of the specimens in FIG. 4.

In FIG. 4, which shows a section along line 4—4 of FIG. 3; the same designations are inserted. In addition, the figure shows a bushing 64 for an electric conductor through the specimens 3. From the half 18 of the last specimen 3, a return conductor 65 passes through a bushing (not shown) back to a voltage source 69 (see FIG. 9). The indicated conductors 66, 67 and 68 from the halves 16 of the specimens 3 also pass through bushings and voltmeters (not shown) back to the same voltage source 69. The circuit diagram for this indication is shown in FIG. 9, in which the same designations as in FIG. 4 are introduced. The voltmeters are designated 70, 71 and 72, and the bushings not shown in FIG. 4 are designated 73. 74 designates a resistor. In case of a rupture in, for example, the central test body 3, the voltmeter 71 indicates this.

Figure 6:
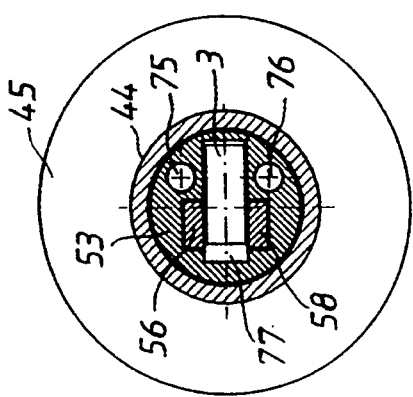
FIG. 6 shows a section along line 6—6 of FIG. 3.
Figure 5:
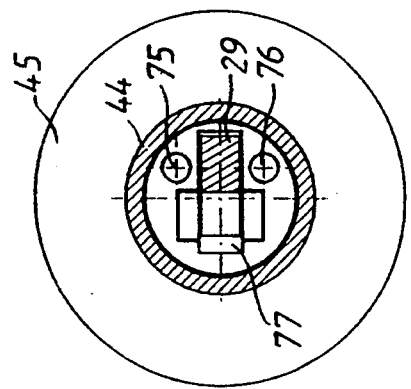
FIG. 5 shows a section along line 5—5 of FIG. 3.

FIGS. 5-7 are sections along lines 5—5, 6—6 and 7—7 of FIG. 3 and show, inter alia, how the spacing sleeves 53 are designed to secure the connection between the pipe 41 and the space 54 via, inter alia, channels 75, 76 and 77.

The testing device 42 operates in the same way as the testing device 2 by conveying the pressure-carrying medium into the first space 54 via the pitot tube 61 and the channel 77 and out through the channels 75 and 76 as well as the pitot tubes 62 and 63. The pressure in the second space 52 is assumed to be atmospheric pressure and thereby the high system pressure in the pipe 41 causes the specimens 3 to be subjected to load in the same way as the specimen 3 in the testing device 2. In the same way as before, a part of the testing device 42 can also be detached from the flange 45 and be withdrawn from the nuclear reactor with all the enclosed specimens 3. Finally, it can be noted that the specimen 3, for example, can be formed from the same material as is present in the pipe system, thus obtaining a valuable test of the strength of the pipe system.

I claim:

1. A device for load-testing of specimens (3) in a nuclear reactor environment, characterized in that at one of the pipes (1) of the nuclear reactor for conveying a first medium under pressure, there is fixed a testing device (2) comprising a first space (14) in open communication with said pipe (1), a movable pull rod (15) arranged in said first space (14), one end of said pull rod (15) being intended to be attached to one half (16) of a specimen (3) arranged in the space (14), the other end of said pull rod (15) being joined to a tensile force device, capable of being influenced by the first medium, for achieving a tensile stress in the specimen (3) via the pull rod (15).

2. A device according to claim 1, characterized in that the testing device (2) comprises a first sleeve (13, 6, 8), connected to the pipe (1) in open communication, and an extension, which is movable in relation to the first sleeve, in the form of a second sleeve (9), said sleeves together surrounding at least part of said first space (14), a pull rod (15) arranged in said first space (14) with one end fixed to the movable second sleeve (9), the other end of the pull rod (15) being adapted to be attached to one half (16) of a specimen (3) fixed in the space (14), said second sleeve (9) being adapted to be influenced by a first medium supplied from the pipe (1) in order to achieve a tensile stress in the specimen (3) via the pull rod (15).

3. A device according to claim 2, characterized in that the first and second sleeves are interconnected by means of a bellows (10), said second sleeve (9) and bellows (10) being surrounded by a third sleeve (11) forming a second space (12) around said second sleeve (9) and the bellows (10), said second sleeve (12) containing or being connectable to a second medium of lower pressure than said first medium.

4. A device according to claim 3, characterized in that said second space (12) is also connectable to a medium of the same or a higher pressure in relation to said first medium.

5. A device according to claim 1 or 2, characterized in that several specimens (3) are connected in series in said first space (54).

6. A device according to claim 1 or 2, characterized in that the testing device (2, 42) is detachably attached to said pipe (1, 41).

* * * * *